US006386197B1

(12) United States Patent
Miller

(10) Patent No.: US 6,386,197 B1
(45) Date of Patent: May 14, 2002

(54) NASAL AIR PASSAGEWAY OPENING DEVICE

(75) Inventor: Brooke Daniel Miller, Anaheim, CA (US)

(73) Assignee: Brook D. Miller, Anaheim, CA (US)

( * ) Notice: Subject to any disclaimer, the term of this patent is extended or adjusted under 35 U.S.C. 154(b) by 0 days.

(21) Appl. No.: 09/491,725

(22) Filed: Jan. 27, 2000

(51) Int. Cl.$^7$ .............................................. A61M 15/08
(52) U.S. Cl. ........................... 128/206.11; 128/207.18; 128/200.24
(58) Field of Search ...................... 128/200.24, 207.18, 128/848, 857, 858, 912, DIG. 26, 206.11; 606/199, 191, 196, 204.15, 204.45; 602/46, 47

(56) References Cited

U.S. PATENT DOCUMENTS

| | | | | |
|---|---|---|---|---|
| 1,256,188 A | * | 2/1918 | Wilson | |
| 2,087,042 A | * | 7/1937 | Phillips | 128/148 |
| 2,215,188 A | * | 9/1940 | Parks | 128/198 |
| 2,274,997 A | * | 3/1942 | Thurman | 128/132 |
| 2,335,936 A | * | 12/1943 | Hanlon | 128/342 |
| 2,433,565 A | * | 12/1947 | Korman | 128/148 |
| 2,569,743 A | * | 10/1951 | Carlock | 128/148 |
| 2,672,138 A | * | 3/1954 | Carlock | 128/148 |
| 2,890,695 A | * | 6/1959 | Safstrom | 128/148 |
| 3,722,509 A | * | 3/1973 | Nebel | 128/140 N |
| 3,747,597 A | * | 7/1973 | Olivera | 128/140 N |
| 3,905,335 A | * | 9/1975 | Kapp | 128/140 N |
| 4,030,491 A | * | 6/1977 | Mattila | 128/140 N |
| 4,052,983 A | * | 10/1977 | Bovender | 128/140 N |
| 4,221,217 A | * | 9/1980 | Amezcua | 128/206.11 |
| 4,267,831 A | * | 5/1981 | Aguilar | 128/203.14 |
| 4,782,832 A | * | 11/1988 | Trimble et al. | 128/207.18 |
| 5,117,820 A | * | 6/1992 | Robitaille | 128/206.11 |
| 5,665,104 A | * | 9/1997 | Lee | 606/199 |
| 5,775,335 A | * | 7/1998 | Seal | 128/848 |
| 5,890,491 A | * | 4/1999 | Rimkus | 128/206.11 |
| 5,931,852 A | * | 8/1999 | Brennan | 606/199 |
| 6,004,342 A | * | 12/1999 | Filis | 606/199 |

* cited by examiner

Primary Examiner—Glenn K. Dawson
Assistant Examiner—Mital Patel
(74) Attorney, Agent, or Firm—Stout, Uxa, Buyan & Mullins LLP

(57) ABSTRACT

A nasal passageway opening device including a body defining an airflow channel therethrough for insertion in the nasal passageway. The body may be conical, and may include a plurality of external protrusions to increase frictional resistance with the nasal passageway. The body may be solid, or hollow to incorporate a medicament therein, such as a mentholated gel. If the body is hollow, the interior surface may include a plurality of apertures for release of the medicament. The device is positioned within the nasal passage a sufficient distance so that it is hidden from view, thus illuminating the need for unsightly external nasal strips or topical applications of odiferous mentholated gels.

20 Claims, 3 Drawing Sheets

NASAL AIR PASSAGEWAY OPENING DEVICE

FIELD OF THE INVENTION

The present invention relates to devices for clearing blocked nasal passages and, more particularly, to a nasal air passageway opening device adapted to fit within the nasal passage.

BACKGROUND OF THE INVENTION

Everybody suffers from blocked nasal passages at one time or another. Congestion and stuffy noses are symptomatic of colds, influenza, hay fever, allergies, and other common maladies. More serious sinus problems, such as deviated septums, also may cause nasal congestion and/or constriction of the nasal passage. This general condition is shown in FIG. 1 in which a constriction 20 within the nasal passage 24 reduces airflow therethrough, and even results in complete blockage as indicated by the flow arrows 26.

Various means are available for relieving nasal congestion, ranging from the time-tested remedy of a topical mentholated rub to the more extreme solution of surgery. All of these methods suffer from unique drawbacks.

Although a topical mentholated rub may prove effective for minor or temporary nasal congestions, it is generally insufficient to treat more serious sinus conditions. In addition, the mentholated rub emits a relatively strong odor that may be offensive in daily interpersonal contacts.

Another relatively simple solution that has been successfully marketed is external nasal strips that are placed on the exterior bridge portion of the user's nose. The nasal strip includes some type of therapeutic medication which is continuously inhaled through the nose to treat the blockage. Unfortunately, the nasal strips are relatively unsightly and many users are embarrassed to use them in public. In addition, nasal strips are not re-usable; that is, once removed, one cannot re-attach them. Most nasal strips are manufactured with an adhesive side, similar to BAND-AIDS. As with all such strips, once removed, the adhesive loses its effectiveness. Moreover, many people have relatively oily skin which interferes with an effective adhesion in the first instance. Therefore, the consumer, especially those with oily skin, must carry around a supply of nasal strips for use during the day.

Various other topical and orally-or nasally-administered medications are available for relieving sinus congestion. Unfortunately, use of such medications for chronic sinus congestion may cause negative side effects. For example, most sinus medications make the user drowsy, which limits the periods of use. More significantly, repeated use of some sinus medications may cause a buildup of toxins in the kidneys, which forces them to work harder, and may even result in long-term kidney damage requiring dialysis.

A deviated nasal septum is a genetic condition in which the nasal air passage has not developed normally. In other words, the walls of the nasal passages are positioned closer together to restrict airflow therethrough. This condition causes sinus pressure, headaches, dizziness, and at the very least stuffy noses. Again, over-the-counter medications provide little or no relief, and may actually cause more serious problems. A corrective surgical procedure may be recommended by an ear, nose and throat doctor. Unfortunately, the surgery may not be entirely effective, and may result in scar tissue forming inside the nose which perpetuates the problem. Sometimes a second surgery to remove the scar tissue is recommended, although again the surgery may not work. Moreover, surgery to correct a deviated septum is relatively painful.

Therefore, there is a need for a device for treating blocked nasal passages that is effective, comfortable and socially acceptable, and which reduces the need for potentially harmful long-term use of medications and surgery.

SUMMARY OF THE INVENTION

Various objects and advantages are provided by the present invention, including:

A device to provide fast, safe and effective relief from nasal sinus pressure.

A device that promotes nasal sinus drainage.

A device that provides an inexpensive and safe alternative to medications and inhalants.

An over-the-counter sinus congestion relief product eliminating the need for a prescription.

A device that provides a safe and effective alternative to corrective surgeries.

A sinus pressure relief device available in a variety of forms for sinus pressure sufferers of different ages.

A device that provides an effective way of obtaining sinus pressure relief without the embarrassment of wearing an external nasal strip, or an odiferous topical medication.

A nasal sinus pressure relief device insertable in the nasal passage that incorporates a mentholated gel.

In one aspect, the invention provides a nasal passageway opening device comprising a body having an exterior surface and interior surface. The interior surface defines an airflow channel therethrough, and the body is sized to fit within a nasal passageway of a wearer to ensure adequate airflow therethrough. Desirably, the body is conical. The body may be solid or hollow and define a cavity between the exterior and interior surfaces. A medicament may be positioned within the cavity, and a plurality of apertures formed in the interior surface permit evaporation and delivery of the medicament. A plurality of protrusions are desirably provided on the exterior surface, primarily to increase frictional resistance with the nasal passageway.

In another form, the invention provides a nasal passageway opening device, including a body sized to fit within a nasal passageway of a wearer, the body defining an airflow channel therethrough. A medicament is incorporated into the body and is in communication with the airflow channel for release of vapor to the wearer. The body may include an interior wall having a plurality of apertures, an exterior wall, and a cavity therebetween, the medicament being positioned within the cavity. The body may be conical or other wise.

A further understanding of the nature and advantages of the invention will become apparent by reference to the remaining portions of the specification and drawings.

DESCRIPTION OF THE PREFERRED EMBODIMENTS

The present invention provides a nasal sinus pressure relief device that can be inserted in the nasal passage to improve airflow therethrough. Various shapes, surface textures, and functional aspects are described herein, but should not be considered limiting. For example, the invention contemplates a conical device to help in positioning the device in the nasal passage, but a tubular shape may be equally effective, although slightly more difficult to correctly position. Additionally, the various embodiments described herein include a single airflow channel therethrough, but those of skill in the art will understand that inner walls may be provided to divide the airflow passage into two or more channels.

Figure 2:
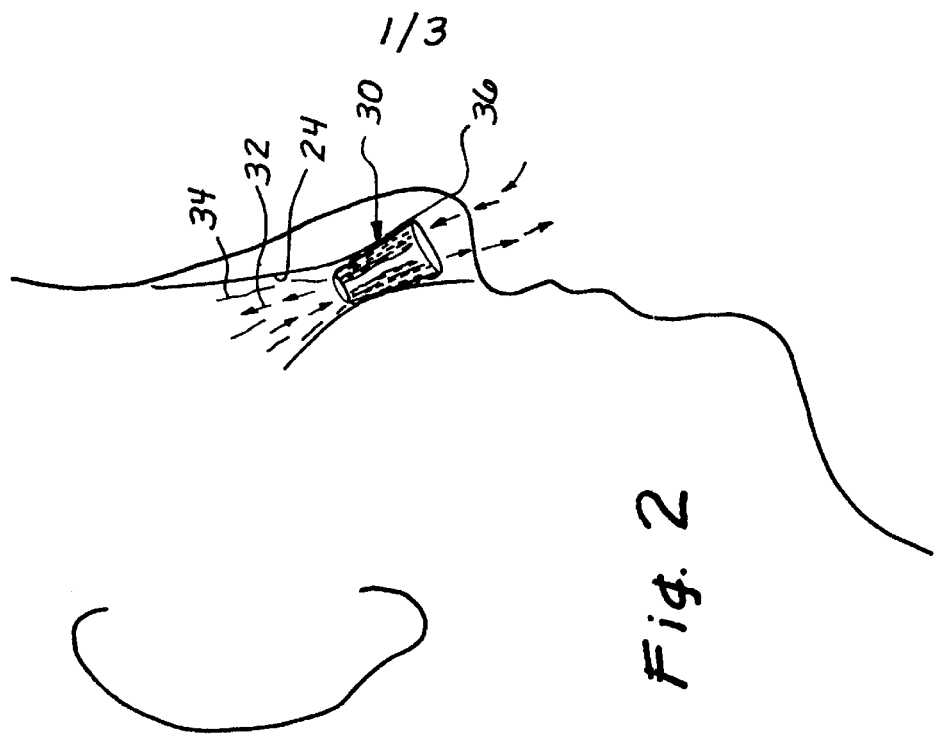
FIG. 2 is a schematic view of a sinus pressure relief device inserted in the nose to treat a constricted nasal passage.
Figure 1:
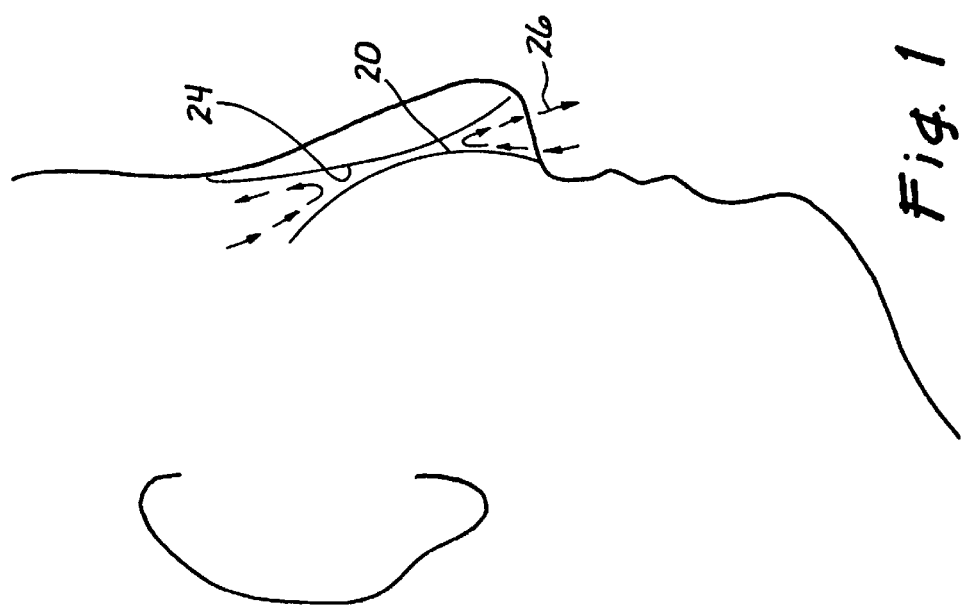
FIG. 1 is a schematic view of a constricted nasal passage.

With reference to FIG. 2, an exemplary sinus pressure relief device 30 is shown inserted into the nasal passage 24 of FIG. 1 at the approximate location of the constriction 20. The device 30, as described more detail below, opens the constriction 20 and provides an airflow channel therethrough. As seen by the arrows 32, proper airflow results. Furthermore, the device 30 may incorporate a medication, such as a mentholated gel, and a therapeutic vapor 34 can be administered by the device directly into the sinus cavities located above the nasal passage 24 without propagating to the surrounding environment.

Importantly, the device 30 is desirably sized to be positioned sufficiently far from the nasal passage opening 36 so as to be hidden from view. Therefore, the wearer of the device 30 may go out in public without the embarrassment sometimes associated with external nasal strips. To insure such advantageous positioning, the device 30 is desirably manufactured in a number of sizes for different sized nasal passages 24, or different levels of constriction 20. That is, a small child may require a smaller-sized device 30 band would a full-grown adult. A conical shape is preferred for its tendency to wedge into a correct position, but still enable easy removal.

Figure 3A:
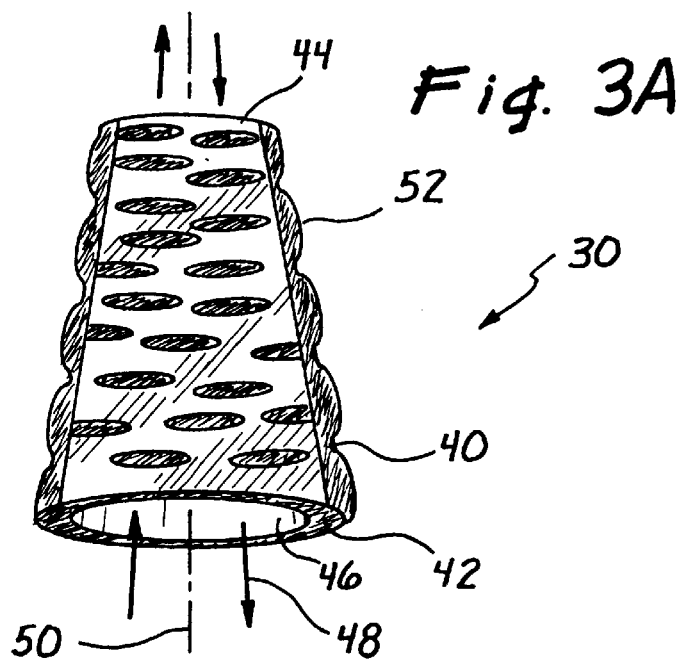
FIG. 3A is an elevational view of an exemplary embodiment of the sinus pressure relief device of the present invention.
Figure 3B:
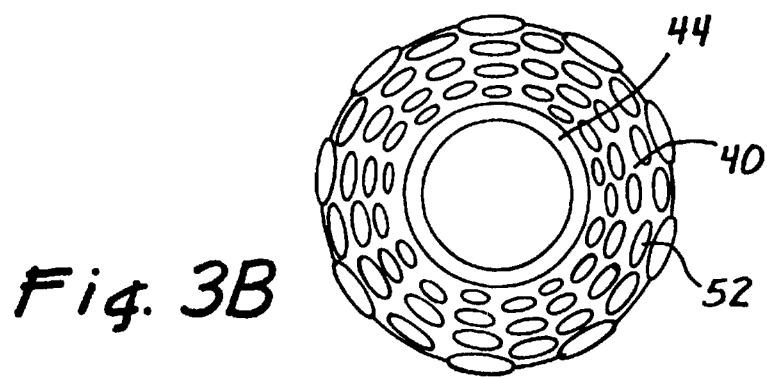
FIGS. 3B and 3C are top and bottom plan views, respectively, of the device of FIG. 3A.
Figure 3C:
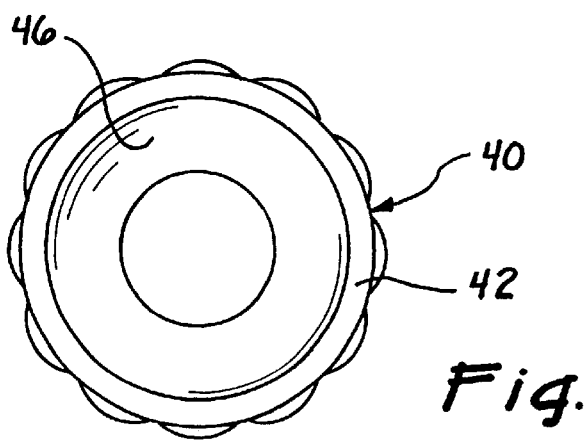

FIGS. 3A–3C illustrate one embodiment of the sinus pressure relief device 30 of the present invention. The device 30 comprises a hollow conical body 40 having a first end and associated first mouth 42, and a second end and associated second mouth 44 that is smaller than the first mouth. Because of the conical shape of the body 40, both the first and second mouths 42, 44 are circular. A conical interior wall 46 of the body 40 defines a single airflow channel therethrough, as indicated by the arrows 48.

In a preferred embodiment, the device 30 is aligned about an axis 50 so that the first and second mouths 42, 44 are concentric about the axis. Alternatively, the body 40 may extend in a curvilinear path so that the first and second mouths 42, 44 are offset for one another. Such a curved device 30 may be desired for irregularly-shaped nasal passages, such as with those with broken noses prior to corrective surgery. As mentioned above, in either the straight or curved configuration, the device 30 may have a first end larger than the second end, as shown, or the device may be tubular with the first and second ends being identically sized.

In a preferred embodiment, as seen in FIGS. 3A–3C, the exterior surface of the body 40 is covered in a plurality of bumps or corrugations 52. As shown, the corrugations 52 comprise oval-shaped outward projections from the otherwise smooth, conical exterior surface of the body 40. In a preferred embodiment, the major axis of each of the oval-shaped corrugations 52 is oriented generally laterally with respect to the central axis 50 to increase frictional resistance with the interior of the nasal passage 24, often in conjunction with the nasal hair of the wearer. In addition, the corrugations 52 are of a sufficient height so as to create spaces between the body 40 and nasal passage 24 and permit some airflow therethrough. The spaces thus created further help to retain the device 30 within the nasal passage 24 by permitting moisture exuded from the nasal passage walls to drain.

Other configurations of the corrugations 52 may be substituted, such as for example, hemispherical or oval-shaped with the major axis aligned generally axially to further facilitate airflow around the device 30. In each instance, the corrugations 52 are desirably rounded, or otherwise do not exhibit sharp edges, to reduce any discomfort to the wearer. Of course, the corrugations 52 are optional, and the exterior of the device 30 may be smooth if desired.

In addition to or in lieu of the corrugations 52, flexible, porous or absorbent material may be provided on the exterior of the device 30. For example, the exterior surface of the body 40 main be covered with a layer of cotton, or other material as a cushion of sorts to increase comfort to the wearer. An absorbent layer may be provided around the body 40 to help reduce the runny nose symptom of colds and flu, for example.

The device 30 can be made a number of materials, flexible or otherwise. For example, the device 30 may be made of a rubber, PTFE, or other relatively soft polymer. Preferably, the device is elastomeric (e.g., rubber) for maximum comfort. Alternatively, the device 30 may be made of a more rigid plastic or of fiberglass. If the device is rigid, a soft layer around the exterior of the device is desirably provided for the wearer's comfort.

As seen in FIG. 2, the sinus pressure relief device 30 is used by inserting it into nasal passage 24 to the region of a constriction. It is best to first clear the nostrils of excess mucus to avoid inadvertently plugging the interior channel. The device 30 is intended to relieve the symptoms of nasal constriction for a period of between 1–12 hours, depending on the severity of congestion and certain other factors.

Figure 4:
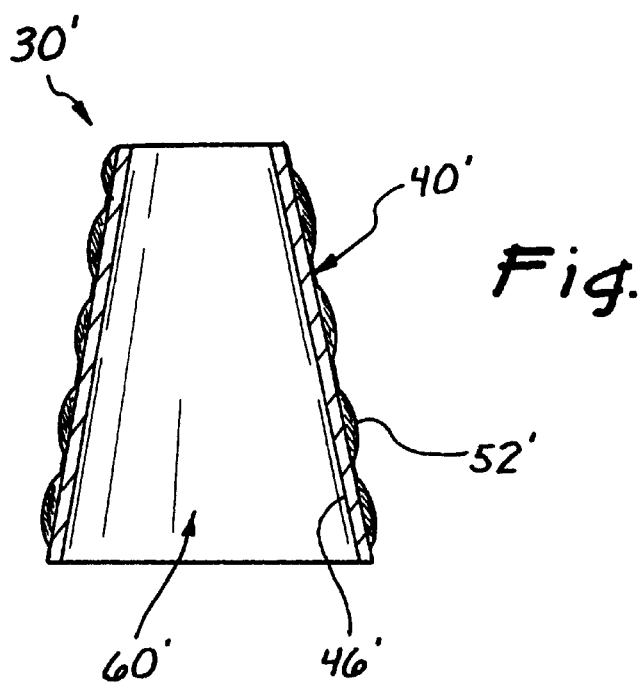
FIG. 4 is a cross-sectional view through one embodiment of a sinus pressure relief device of the present invention.

FIG. 4 illustrates one exemplary cross-section of a device 30' of the present invention. In this is simplified embodiment, the body 40' comprises a solid conical material having an exterior surface with a plurality of corrugations 52' thereon, and an interior conical surface 46 defining a single airflow channel 60 therein.

Figure 5:
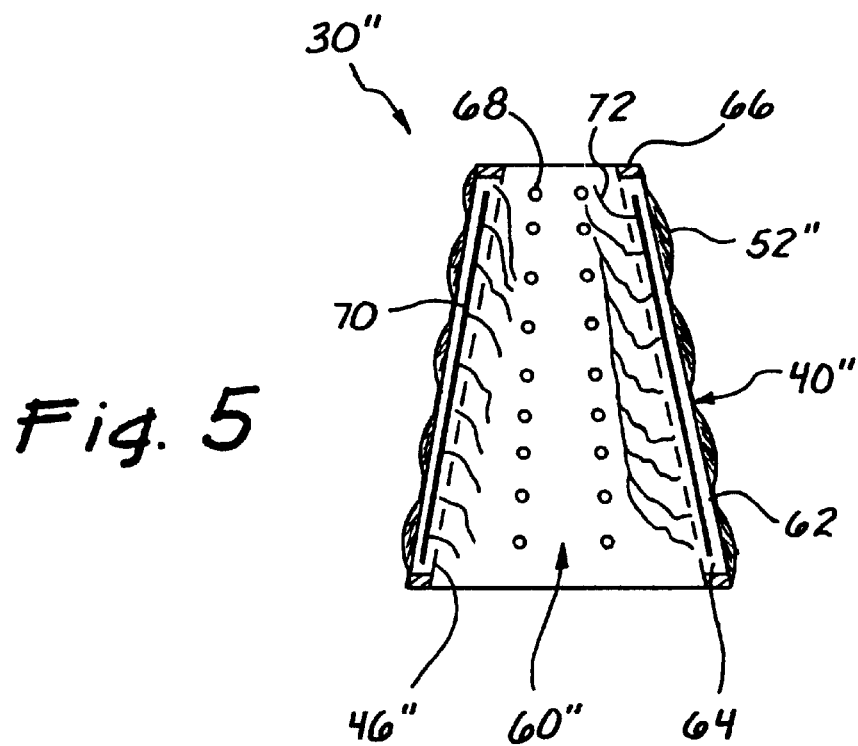
FIG. 5 is a cross-sectional view through another embodiment of a sinus pressure relief device of the present invention incorporating a medicament.

FIG. 5 illustrates a further exemplary cross-section of the device 30" that incorporates a medicament. More particularly, the device 30" is defined by a hollow conical body 40" having an exterior wall 62 and interior wall 46". The interior wall 46" is radially spaced from the exterior wall 62 to define a conical cavity 64 therebetween. Both ends of the conical cavity 64 may be closed using annular plugs, such as seen at 66. A series of small apertures 68 are formed in the interior wall 46". The apertures 68 may be in a variety of configurations, including in a series of axial rows as shown. As before, a series of corrugations 52 are desirably provided on the exterior of the body 40".

The conical cavity 64 contains a medicament 70, such as a mentholated gel. The medicament 70' is exposed to the interior channel 60" via the apertures 68. In this manner, vapor 72 from evaporation of the medicament 70 escapes into the channel 60" for inhalation by the user. The medicament 70 may be in gel form, or may be a conical absorbent plug saturated with a medicament. Desirably, the apertures 68 are small enough so that the medicament 70, if in gel form, will not extrude into the channel 60". In the device 30" of FIG. 5, therefore, an appropriate medication may be applied to the wearer's sinuses without the embarrassment of an external nasal strip, or the inconvenience of a topical application of mentholated gel.

While the foregoing is a complete description of the preferred embodiments of the invention, various alternatives, modifications, and equivalents may be used. It will be obvious that certain other modifications may be practiced within the scope of the appended claims.

What is claimed is:

1. A nasal passageway opening device, comprising:
   a body having a first end, a second end, and a longitudinal axis extending through the body from the first end to the second end, the body further having an exterior surface and an interior surface, the interior surface defining an airflow channel extending through the body from the first end to the second end, the body being sized and shaped to fit within a nasal passageway of a wearer to ensure adequate airflow through the nasal passageway when the nasal passageway opening device is filled within the nasal passageway; and
   a cavity formed within the body between the exterior surface and the interior surface, the cavity being disposed radially outwardly of the airflow channel and being separated from the airflow channel by the interior surface.

2. The device of claim 1, wherein the body is conical.

3. The device of claim 2, wherein the cavity at least partially encircles the airflow channel.

4. The device of claim 3, wherein the cavity extends from the first end to the second end.

5. The device of claim 4, further including a medicament positioned within the cavity, and a plurality of apertures formed in the interior surface, the plurality of apertures fluidly connecting the airflow channel to the cavity.

6. The device of claim 4, further including a plurality of protrusions on the exterior surface.

7. The device of claim 6, wherein the protrusions have oval cross sections.

8. The device of claim 1, wherein the cavity encircles the airflow channel.

9. The device of claim 8, further comprising a plurality of apertures formed in the interior surface, the plurality of apertures fluidly connecting the airflow channel to the cavity.

10. The device of claim 9, further including a medicament positioned within the cavity.

11. The device of claim 10, further including a plurality of protrusions on the exterior surface.

12. The device of claim 11, wherein the protrusions are oval-shaped.

13. The device of claim 1, wherein the cavity is conical.

14. The device of claim 13, wherein the cavity is cylindrical.

15. The device of claim 1, wherein the body is rigid.

16. The device of claim 15, wherein the nasal passageway opening device is adapted to be fitted entirely within the nasal passageway.

17. A nasal passageway opening device, comprising:
    a body having a first end, a second end, and a longitudinal axis extending through the body from the first end to the second end, the body further having an exterior surface and an interior surface, the interior surface defining an airflow channel extending through the body from the first end to the second end, the body being sized and shaped to fit within a nasal passageway of a wearer, and the body further being adapted to ensure adequate airflow through the nasal passageway when the nasal passageway opening device is fitted within the nasal passageway; and
    a cavity disposed between the interior surface and the exterior surface;
    wherein the interior surface surrounds but does not obstruct the airflow channel, the exterior surface surrounds the interior surface and comprises a plurality of apertures, and the cavity is in fluid communication with the airflow channel.

18. The device of claim 17, wherein:
    the device further comprises a plurality of bumps on the exterior surface of the body; and
    a major axis of each of the plurality of bumps is oriented generally laterally with respect to the longitudinal axis of the body to thereby increase frictional resistance of the nasal passageway opening device with an interior of the nasal passageway.

19. The device of claim 17, wherein a medicament is disposed within the cavity.

20. The device of claim 17, wherein the body is conical.

* * * * *

UNITED STATES PATENT AND TRADEMARK OFFICE
CERTIFICATE OF CORRECTION

PATENT NO.    : 6,386,197 B1
DATED         : May 14, 2002
INVENTOR(S)   : Brooke D. Miller It is certified that error appears in the above-identified patent and that said Letters Patent is hereby corrected as shown below:

Title page,
Item [73], Assignee: "Brooke D. Miller, Anaheim, CA (US)" should read
-- Brooke D. Miller, 1212 East Haven Drive, Anaheim, CA 92805 (US) --.
Item [75], Inventor: "Brooke D. Miller, Anaheim, CA (US)" should read
-- Brooke D. Miller, 1212 East Haven Drive, Anaheim, CA 92805 (US) --.

Column 3,
Line 22, "described more" should read -- described in more --.
Line 55, "offset for one" should read -- offset from one --.

Column 4,
Line 24, "40 main be" should read -- 40 may be --.
Line 45, "this is simplified" should read -- this simplified --.
Line 48, "surface 46, defining" should read -- surface 46' defining --.
Line 49, "channel 60 therein." should read -- channel 60' therein. --.
Line 60, "corrugations 52 are" should read -- corrugations 52" are --.
Line 63, "medicament 70' is" should rad -- medicament 70 is --.

Column 5,
Line 25, "is filled within" should read -- is fitted within --.

Signed and Sealed this

Twenty-sixth Day of November, 2002

Attest:

JAMES E. ROGAN
Attesting Officer
Director of the United States Patent and Trademark Office